Figure 3:
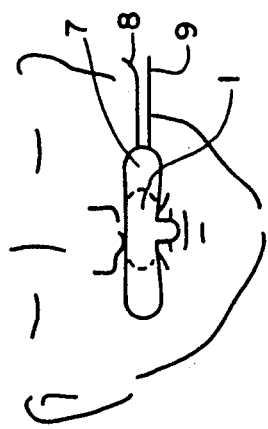

United States Patent [19]

Malkamäki

[11] Patent Number: 5,195,529
[45] Date of Patent: Mar. 23, 1993

[54] SENSOR FOR MONITORING RESPIRATION

[75] Inventor: Lauri Malkamäki, Salem, N.H.

[73] Assignee: Instrumentarium Corporation, Finland

[21] Appl. No.: 603,478

[22] Filed: Oct. 25, 1990

[30] Foreign Application Priority Data

Oct. 27, 1989 [FI] Finland ............... 895131

[51] Int. Cl.⁵ ............................................. A61B 5/087
[52] U.S. Cl. ..................................... 128/716; 128/725
[58] Field of Search ........ 128/716, 725, 671, 639–640, 128/734; 73/861.09, 29.01–29.03, 335

[56] References Cited

U.S. PATENT DOCUMENTS

| 2,681,571 | 6/1954 | Becker | 73/29.01 |
| 3,559,456 | 2/1971 | Lomker et al. | 73/29.02 |
| 3,954,100 | 5/1976 | Sem-Jacobsen | 128/639 |
| 4,328,478 | 5/1982 | Murata et al. | 73/335 |
| 4,496,931 | 1/1985 | Watanabe et al. | 73/335 |
| 4,497,701 | 2/1985 | Murata et al. | 73/335 |
| 4,520,341 | 5/1985 | Miyoshi et al. | 73/335 |
| 4,539,996 | 9/1985 | Engel | 128/640 |

Primary Examiner—Lee S. Cohen
Assistant Examiner—Jeffrey R. Jastrzab
Attorney, Agent, or Firm—Andrus, Sceales, Starke & Sawall

[57] ABSTRACT

For monitoring respiration occurring through the respiratory tract or tracts of a patient, a sensor comprises two spaced-apart electrically conductive elements (2,3). Wires (8,9) extend from the elements to a measuring instrument. The transfer of an electrical charge between the elements is effected by means of charge carriers in an intermediate layer between the electrically conductive elements and responsive to moisture in respired air. The transfer provides an indication of respiration to a measuring instrument.

28 Claims, 1 Drawing Sheet

U.S. Patent  Mar. 23, 1993  5,195,529

SENSOR FOR MONITORING RESPIRATION

The present invention relates to a sensor means adapted to the monitoring of respiration occurring through the respiratory tract or tracts of a patient.

Generally, the monitoring methods for the respiration of a patient are based on the thoracic movement or the variations of pulmonary capacity during respiration. Pressure sensors attached to the skin are used to observe the thoracic movement. A piezoelectric membrane, which also detects the thoracic movement, has been used for the observation of respiration. On the other hand, impedance sensors are employed for measuring variations in respiratory capacity. However, measurements effected on these principles are highly sensitive to artifact as all muscular movements are included in measuring results, making the interpretation of results that much more difficult.

In addition, these methods must be considered unreliable as they monitor the respiratory movements of a patient which may still continue even if the passage of air into the lungs is blocked e.g. as a result of air accumulated in the respiratory tracts. Not until the respiratory movements have ceased and the oxygen supply of a patient has already been blocked for some time will these methods be capable of providing information on this serious condition. Thus, this must be regarded as a very significant problem.

In principle, there is available a more reliable method which is based on monitoring the flow of air by means of thermistors. The operation of thermistors is based on the change in resistance value as a result of the change in temperature. A drawback in such a thermistor is its rather inconvenient structural design. Another problem associated with inexpensive thermistors is limited sensitivity. In measurement, problems are caused by moisture. If the mucus separating from the respiratory tracts of a patient for some reason or another ends up on a thermistor, the result will be a measuring fault. The position of a thermistor in front of the respiratory tract is extremely critical. Thus, it must be positioned exactly right for detecting a respiratory signal. Therefore, the installation of a thermistor requires a lot of work.

An object of this invention is to eliminate the above problems. The object is to provide a sensor means having a simple design and inexpensive price. Another object is to provide a sensor means for reliably picking up a respiratory signal directly from the alveolar air-flow.

The characterizing features of a device of the invention are set forth in the annexed claims.

The invention utilizes an electrochemical couple formed by an electrically conductive material as well as the moisture of alveolar air. The establishment of such a couple requires two separate electrically conductive elements which are in mutual electrical contact through the intermediary of charge carriers, such as ions. The electrically conductive elements may comprise e.g. magnesium or preferably aluminium or mixtures thereof. Some other metal can also be appropriate. The separate electrically conductive elements can even be made of one and the same material. In this case, the voltage can be of either polarity since either element can serve as an anode while the other acts as a cathode.

An advantage gained by using the same material in each element is the fact that it does not matter which way to attach the wires extending to an instrument to be monitored. The polar ambiguity can be eliminated by biasing the electrochemical couple. Thus, the current of an electrochemical couple generated in synchronization with respiration always proceeds in the same direction.

The transfer of an electric charge between the separate elements must be effected by means of charge-carrying ions. Therefore, the elements are connected to each other by means of a material, such as plastic, which permits the transfer of charge-carrying ions from one element to the other as a result of moisture. The elements can even be glued on either side of a piece of plastic. Several polymer-based materials, such as plastics and adhesives, have ions present e.g. from sodium chloride, said ions serving as charge carriers.

A contact between a moist alveolar air-flow and such a sensor means produces an electrochemical couple through the action of the electrically conductive elements and ions establishing a contact between the elements, said couple generating a small voltage between the elements. The voltage signal is further passed to an instrument to be monitored for output.

A sensor means of the invention is particularly preferred for monitoring an air-flow passing through the respiratory tracts e.g. in comparison with a thermistor as it is not sensitive to moisture or skin contact and is thus unlike a thermistor. A liquid excretion issuing from the respiratory tracts and coming into contact with a sensor means of the invention does not lead to a malfunction, since the couple requires an air-flow for its proper operation.

The position of a sensor means of the invention in front of the respiratory tracts is not as critical as in the case of a thermistor since the active surface area of the sensor means is spread over a larger area.

Figure 2:
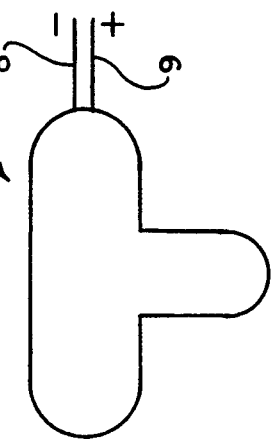
Figure 1:
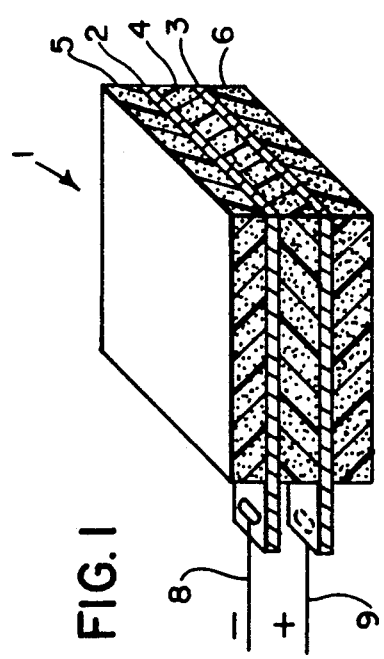
Figure 4:
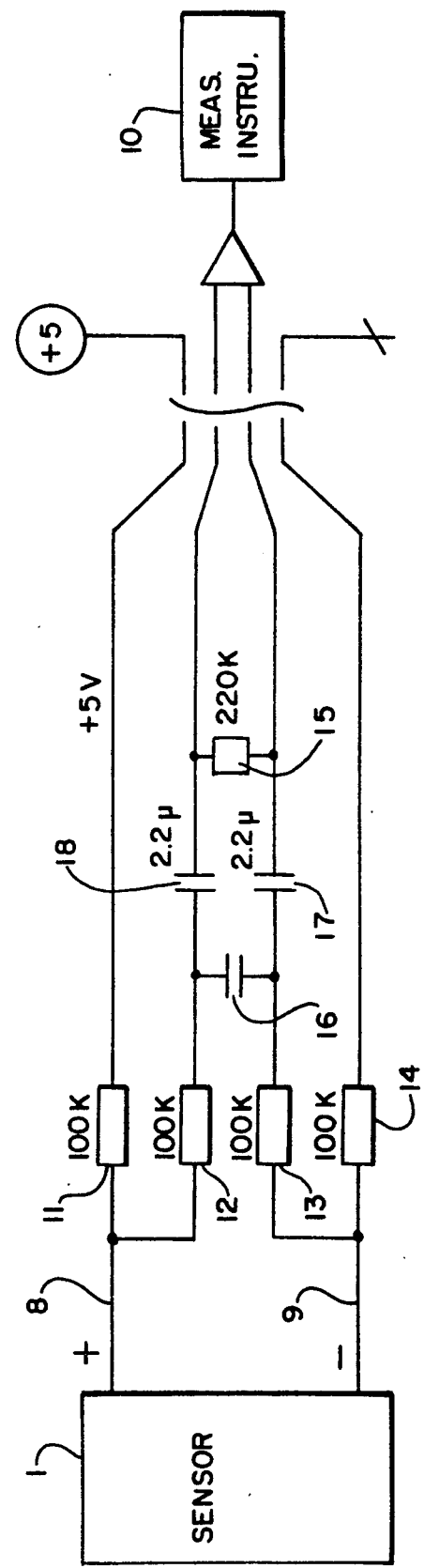

The invention will now be described in more detail with reference made to the accompanying drawings, in which FIG. 1 shows a perspective view of a sensor means of the invention, FIG. 2 shows one embodiment of the sensor means of FIG. 1 for detecting both oral and nasal respiration, FIG. 3 shows the sensor means of FIG. 2 attached below the nose of a patient when viewing directly towards the face of a patient, FIG. 4 shows a circuit diagram for connecting a sensor means of FIGS. 1-3 to a monitor.

FIG. 1 shows a perspective view of the most preferred embodiment of a sensor means 1 according to the invention. The sensor means comprises two spaced-apart electrically conductive elements 2 and 3. These elements are also electrochemically reactive. Elements 2 and 3 are preferably made of aluminium. Furthermore, the elements are preferably made of thin foil strips. Between these elements is an intermediate layer 4 which allows the transfer of electric-charge carrying ions from element 2 to element 3 or vice versa. Said intermediate layer is preferably made of a polymer-based material, such as cellular plastic, which at the same time structurally supports the sensor element. Transfer of electric-charge carrying ions from element 2 to element 3, or vice versa occurs as a result of moisture in the intermediate layer. The air exhaled by a patient is moist.

Intermediate layer 4 is preferably fastened to elements 2 and 3 with an adhesive. The reason for this is not only the adhering ability but also the fact that, if the intermediate layer did not contain charge-carrying ions, the adhesive generally contains such ions anyway.

However, the intermediate layer itself must not be electrically conductive. Intermediate layer 4 may be formed out of the Scotch brand foam tape having adhesive on both sides made and sold by the 3-M Corp. of St. Paul, Minn.

Furthermore, the outer sides of elements 2 and 3 furthest away from intermediate layer 4 are protected by an electrically insulating layer 5 and 6 which can also be made of a polymer-based material, such as foam plastic. These layers can also be adhesive-fastened to elements 2 and 3. The surface of insulating layer 5 and 6 coming to contact with the skin should also be preferably provided with an adhesive in order to attach the sensor means directly to the skin of a patient under the nose. The electrically insulating layer could be made of e.g. polyethylene. Air is also a useful insulant. Thus, the actual insulating layers are not required as long as said elements 2 and 3 are not allowed to come into contact with the skin, for example.

FIG. 2 illustrates from above or from below one preferred embodiment of a sensor means which extends from just under the both nostrils all the way to cover the mouth. Otherwise, this sensor means is similar to that of FIG. 1. This embodiment is certain to produce a respiration signal, even if one of the respiratory tracts should be blocked. In order to detect the respiration occurring through the nostrils, the sensor means is provided with a wide upper section, i.e. the edges of electrically conductive elements 2 and 3 and those of intermediate layer 4 will be positioned on the path of alveolar air travelling through both nostrils. The downwardly hanging portion of a sensor means should be positioned in front of the mouth, preferably located as centrally as possible relative to alveolar air-flow. Otherwise the sensor means illustrated in this FIG. 2 is structurally similar to that of FIG. 1.

In this preferred case, the edges of a flat designed sensor means, i.e. the edges of elements 2 and 3 and intermediate layer 4, are uncovered at least over those portions of the edge which are positioned in front of the respiratory tracts. In FIG. 3, a sensor means 1 is attached under the nose of a patient by means of an adhesive tape 7.

When the alveolar air-flow of a patient meets the edge of a sensor means with elements 2 and 3 projecting therefrom, the moisture contained in alveolar air results in the formation of ions originating e.g. from adhesives used in the structure of a sensor means, said ions producing a small voltage between the elements 2, 3. The voltage variations on the sensor means can be used to detect the respiratory rhythm of a patient which is displayed on a monitor. When the detection of voltage is effected by means of a high-impedance voltmeter, the voltage can even exceed 100 mV.

FIG. 4 illustrates one possible circuit diagram for connecting sensor elements 2 and 3 through the intermediary of wires 8 and 9 to a measuring instrument 10. Resistances 11, 12, 13 and 14 are provided for the protection of the patient. Resistances 11 and 14 are also used for supplying the bias voltage to a sensor.

Capacitors 17 and 18 are provided for DC isolation and, together with resistances 15, 12 and 13 as well as a capacitor 16, they determine a frequency response characteristic for the system. However, resistance 15 and capacitor 16 are not necessary for the operation of the instrument.

The invention is by no means limited to the above embodiments but various details of the invention can be modified within the scope of the annexed claims. Elements 2 and 3 are illustrated in the figures as flatshaped foils but, for example, a wire-shaped element would be just as useful. Thus, the invention is by no means limited by the shape of the element.

It is quite obvious that the shape of a sensor means itself can be varied. The sensor means could also be made up by using spaced-apart units located in front of one or several respiratory tracts. The sensor means could also be designed so as to provide a sort of cover mask e.g. in front of the nostrils or both the nostrils and the mouth.

I claim:

1. A sensor for monitoring the respiration of air occurring through one or more respiratory tracts of a patient and for providing an indication of the same to a measuring instrument, said sensor comprising:

two spaced-apart electrically conductive elements (2,3), said elements having means (8,9) for coupling same to the measuring instrument (10);

an intermediate layer means between said elements, said intermediate layer means being capable of transferring electric charge carriers between said elements in the presence of moisture in said intermediate layer means to establish a current between said elements; and means for affixing the sensor to the patient proximate one or more respiratory tracts of the patient to subject the sensor to moisture contained in the air moving during respiration occurring in said one or more tracts.

2. A sensor as set forth in claim 1 wherein said intermediate layer means is further defined as capable of transferring ion electric charge carriers.

3. A sensor as set forth in claim 1 wherein said intermediate layer means is further defined as formed of material which is electrically non-conductive.

4. A sensor as set forth in claim 1 wherein said intermediate layer means includes a cellular plastic material.

5. A sensor as set forth in claim 1 wherein said intermediate layer means includes an adhesive fastening said layer means to said elements.

6. A sensor as set forth in claim 5 wherein said adhesive contains ion electric charge carriers.

7. A sensor as set forth in claim 1 wherein said two electrically-conductive elements are made from different materials.

8. A sensor as set forth in claim 1 wherein said two electrically-conductive elements are made from the same material.

9. A sensor as set forth in claim 8 wherein said sensor further comprises means for applying a bias voltage to one of said elements.

10. A sensor as set forth in claim 1 wherein said elements are substantially planar.

11. A sensor as set forth in claim 1 wherein said elements are formed of a foil material.

12. A sensor as set forth in claim 1 wherein at least one exterior surface of one of said elements is covered with an electrically insulating layer.

13. A sensor as set forth in claim 12 wherein said electrically insulating layer is provided with said means for affixing the sensor to the patient.

14. A sensor for monitoring the respiration of air occurring through the nasal and oral respiratory tracts of a patient and for providing an indication of same to a measuring instrument, said sensor comprising:

two spaced-apart electrically conductive elements (2,3), said elements having means (8,9) for coupling same to the measuring instrument (10); and an intermediate layer means between said elements, said intermediate layer means being capable of transferring electric charge carriers between said elements in the presence of moisture in said intermediate layer means to establish a current between said elements, said sensor having a generally T-shape for being positionable on the upper lip of the patient proximate the nasal and oral respiratory tracts for being subjected to moisture contained in the air moving during respiration occurring in the tracts.

15. A sensor as set forth in claim 14 wherein said elements and layer means are exposed to the respiratory air along edges of said sensor.

16. A sensor as set forth in claim 14 wherein said intermediate layer means is further defined as capable of transferring ion electric charge carriers.

17. A sensor as set forth in claim 14 wherein said intermediate layer means is further defined as formed of material which is electrically non-conductive.

18. A sensor as set forth in claim 14 wherein said intermediate layer means includes a cellular plastic material.

19. A sensor as set forth in claim 14 wherein said intermediate layer means includes an adhesive fastening said layer means to said elements.

20. A sensor as set forth in claim 19 wherein said adhesive contains ion electric charge carriers.

21. A sensor as set forth in claim 14 wherein said two electrically-conductive elements are made from different materials.

22. A sensor as set forth in claim 14 wherein said two electrically-conductive elements are made from the same materials.

23. A sensor as set forth in claim 22 wherein said sensor further comprises means for applying a bias voltage to one of said elements.

24. A sensor as set forth in claim 14 wherein said elements are substantially planar.

25. A sensor as set forth in claim 14 wherein said elements are formed of a foil material.

26. A sensor as set forth in claim 14 further including means for affixing the sensor to the patient.

27. A sensor as set forth in claim 14 wherein at least one exterior surface of one of said elements is covered with an electrically insulating layer.

28. A sensor as set forth in claim 27 wherein said electrically insulating layer is provided with means for affixing the sensor to the patient.

* * * * *